(12) United States Patent
Oishi et al.

(10) Patent No.: US 7,827,847 B2
(45) Date of Patent: Nov. 9, 2010

(54) GAS SENSOR

(75) Inventors: Hidetoshi Oishi, Utsunomiya (JP); Takashi Sasaki, Shioya-gun (JP); Akihiro Suzuki, Utsunomiya (JP); Tsuyoshi Eguchi, Utsunomiya (JP)

(73) Assignee: Honda Motor Co., Ltd, Tokyo (JP)

( * ) Notice: Subject to any disclaimer, the term of this patent is extended or adjusted under 35 U.S.C. 154(b) by 0 days.

(21) Appl. No.: 11/876,414

(22) Filed: Oct. 22, 2007

(65) Prior Publication Data

US 2008/0092628 A1 Apr. 24, 2008

(30) Foreign Application Priority Data

Oct. 24, 2006 (JP) .............................. 2006-288565

(51) Int. Cl.
*G01N 25/00* (2006.01)
(52) U.S. Cl. ....................................................... 73/23.2
(58) Field of Classification Search ................ 73/25.01, 73/31.05, 23.2
See application file for complete search history.

(56) References Cited

U.S. PATENT DOCUMENTS

| | | | | |
|---|---|---|---|---|
| 4,390,869 A * | 6/1983 | Christen et al. | ............. | 340/632 |
| 4,861,557 A * | 8/1989 | McNally | ....................... | 422/97 |
| 5,798,556 A * | 8/1998 | Hughes et al. | ............... | 257/414 |
| 5,879,631 A * | 3/1999 | Wewers et al. | ................ | 422/98 |
| 6,313,638 B1 * | 11/2001 | Sun et al. | ..................... | 324/464 |
| 6,326,228 B1 * | 12/2001 | Hughes et al. | ................ | 438/49 |
| 6,344,174 B1 * | 2/2002 | Miller et al. | .................. | 422/98 |
| 6,453,723 B1 * | 9/2002 | Ichikawa et al. | ............. | 73/23.2 |
| 6,699,376 B2 * | 3/2004 | Naito | ......................... | 204/429 |
| 6,756,016 B2 * | 6/2004 | Miller et al. | .................. | 422/98 |
| 6,911,180 B2 * | 6/2005 | Miller et al. | .................. | 422/94 |
| 7,007,542 B2 * | 3/2006 | Wang et al. | ................. | 73/23.21 |
| 7,041,256 B2 * | 5/2006 | Wang et al. | .................... | 422/94 |
| 7,078,659 B2 * | 7/2006 | Yokoyama et al. | .......... | 219/544 |
| 7,080,545 B2 * | 7/2006 | Dimeo et al. | ............... | 73/31.05 |
| 7,479,255 B2 * | 1/2009 | Otani et al. | .................... | 422/94 |
| 7,526,942 B2 * | 5/2009 | Otani et al. | ................. | 73/25.03 |
| 2002/0070110 A1 * | 6/2002 | Naito | ......................... | 204/426 |
| 2002/0146352 A1 * | 10/2002 | Wang et al. | .................... | 422/96 |
| 2005/0042141 A1 * | 2/2005 | Otani et al. | .................... | 422/98 |
| 2006/0019402 A1 * | 1/2006 | Wang et al. | ................. | 436/151 |
| 2006/0133962 A1 * | 6/2006 | Otani | .......................... | 422/94 |

FOREIGN PATENT DOCUMENTS

| | | | |
|---|---|---|---|
| JP | 61195339 A | * | 8/1986 |
| JP | 8-121754 A | | 5/1996 |
| WO | 2003-042678 A1 | | 5/2003 |

* cited by examiner

*Primary Examiner*—Hezron Williams
*Assistant Examiner*—Rodney T Frank
(74) *Attorney, Agent, or Firm*—Westerman, Hattori, Daniels & Adrian, LLP (57) ABSTRACT

This gas sensor is provided with: a detection element that measures a gas concentration of a detection target gas contained in an examination gas; a substrate having a heating element; and a supporting member that is fixed to the substrate, protrudes from the heating element, and supports the detection element.

8 Claims, 8 Drawing Sheets

GAS SENSOR

BACKGROUND OF THE INVENTION

Priority is claimed on Japanese Patent Application No. 2006-288565, filed Oct. 24, 2006, the contents of which are incorporated herein by reference.

1. Field of the Invention

The present invention relates to a gas sensor.

2. Description of the Related Art

As an example of a conventional gas sensor which detects inflammable gas contained in an examination gas in a high temperature and high humidity environment, a gas sensor is known which is equipped with a heater unit for preventing a detection element from contacting with dew condensation, and thereby preventing producing the dew condensation inside the gas sensor (for example, refer to Japanese Unexamined Patent Application, First Publication No. H08-121754).

In addition, as another conventional gas sensor that is provided in an exhaust system on an oxygen electrode side of a solid polymer membrane fuel cell, and detects hydrogen gas leaked from a fuel electrode side to the oxygen electrode side through a solid polymer electrolyte membrane, a gas sensor is known which is equipped with a heater arranged between an inlet port for the examination gas and the detection element in order to heat the examination gas, and thereby prevents producing the dew condensation in the gas sensor (for example, refer to the specification of PCT Internal Publication No. WO03/042678).

In the above-mentioned conventional gas sensors, while stopping supplying electrical power to the gas sensor, the detection element is heated only by a heat transfer through an atmosphere around the detection element (i.e., the detection element is only heated by a radiation heat generated from the above-mentioned heater unit or the above-mentioned heater). Therefore, there is a case in which the predetermined necessary heating amount for preventing producing dew condensation inside the gas sensor is insufficient, and thereby causing the detection element contacting with the dew condensation. In such a situation, if the electrical power is supplied to the detection element, there may be a problem in which the temperature distribution on a surface of the detection element becomes locally uneven, and thereby causing defects such as destruction of the detection element, deteriorating the sensitivity of the detection element, and the like.

The present invention was made in view of the above-mentioned circumstances, and has an object of providing a gas sensor that can prevent the destruction of the detection element, deteriorating the sensitivity of the detection element, and the like, due to dew condensation.

SUMMARY OF THE INVENTION

The present invention has employed the followings in order to achieve the above-mentioned object.

That is, a gas sensor of the present invention is provided with: a detection element that measures a gas concentration of a detection target gas contained in an examination gas; a substrate having a heating element; and a supporting member that is fixed to the substrate, protrudes from the heating element, and supports the detection element.

According to the gas sensor, the supporting member that supports the detection element is fixed so as to protrude from the heating element provided on the substrate; therefore, it is possible to directly heat the supporting member and the substrate connected to the detection element. Therefore, while stopping the supply of electrical power to the detection element, it is possible to prevent producing dew condensing at the supporting member and the substrate in addition to the detection element itself. Furthermore, even when the dew condensation is produced at other locations in the gas sensor, it is possible to prevent the dew condensation reaching via the supporting member to the detection element.

The supporting member may be made of a metal.

The detection element may have a substantially ball shape, and may be connected to a pair of the supporting member via a lead wire.

In this case, even when supplying electrical power to the detection element is stopped, since the lead wire and the substrate can be directly heated in addition to the detection element itself, it is possible to prevent producing dew condensation thereon. Furthermore, even when the dew condensation is produced at other locations in the gas sensor, it is possible to prevent the dew condensation reaching to the detection element through the supporting element and the lead wire.

A gas inlet port of a gas detection chamber into which the examination gas is introduced may be provided with a heating element having a communication hole. Otherwise, a gas inlet port of a gas detection chamber into which the examination gas is introduced may be provided with a porous heating element.

In these cases, the examination gas will be heated while passing through the heating element having the communication hole or the porous heating element; therefore, it is possible to prevent the temperature of the examination gas introduced into a gas detection chamber from decreasing to equal to or less than the dew point temperature, and thereby preventing producing dew condensation in the gas detection chamber.

It may be arranged such that a surface heater is provided on a surface of the substrate, while a back face heater is provided on a back face of the substrate.

The heating element may be constructed by a PTC thermistor.

It may be arranged such that: a top face of a gas detection chamber into which the examination gas is introduced, is constructed by the substrate; and the supporting member supports the detection element so as to protrude downward from the substrate.

It may be arranged such that an inner surface of a cylinder member that forms the detection chamber is made of a metal plate, and thereby forming an area where a dew condensation is easily produced comparing to another area, at a position away from the detection element.

The inner surface of the metal plate may be covered with a water-repellent layer.

It may be arranged such that: the gas inlet port is provided at the bottom of the gas detection chamber; and an explosion-proof member, the heating element, and a water-repellent filter are arranged in that order from an inside of the gas detection chamber to an outside of the gas detection chamber.

DETAILED DESCRIPTION OF THE INVENTION

A gas sensor according to one embodiment of the present invention will be explained below with reference to the drawings.

Figure 1:
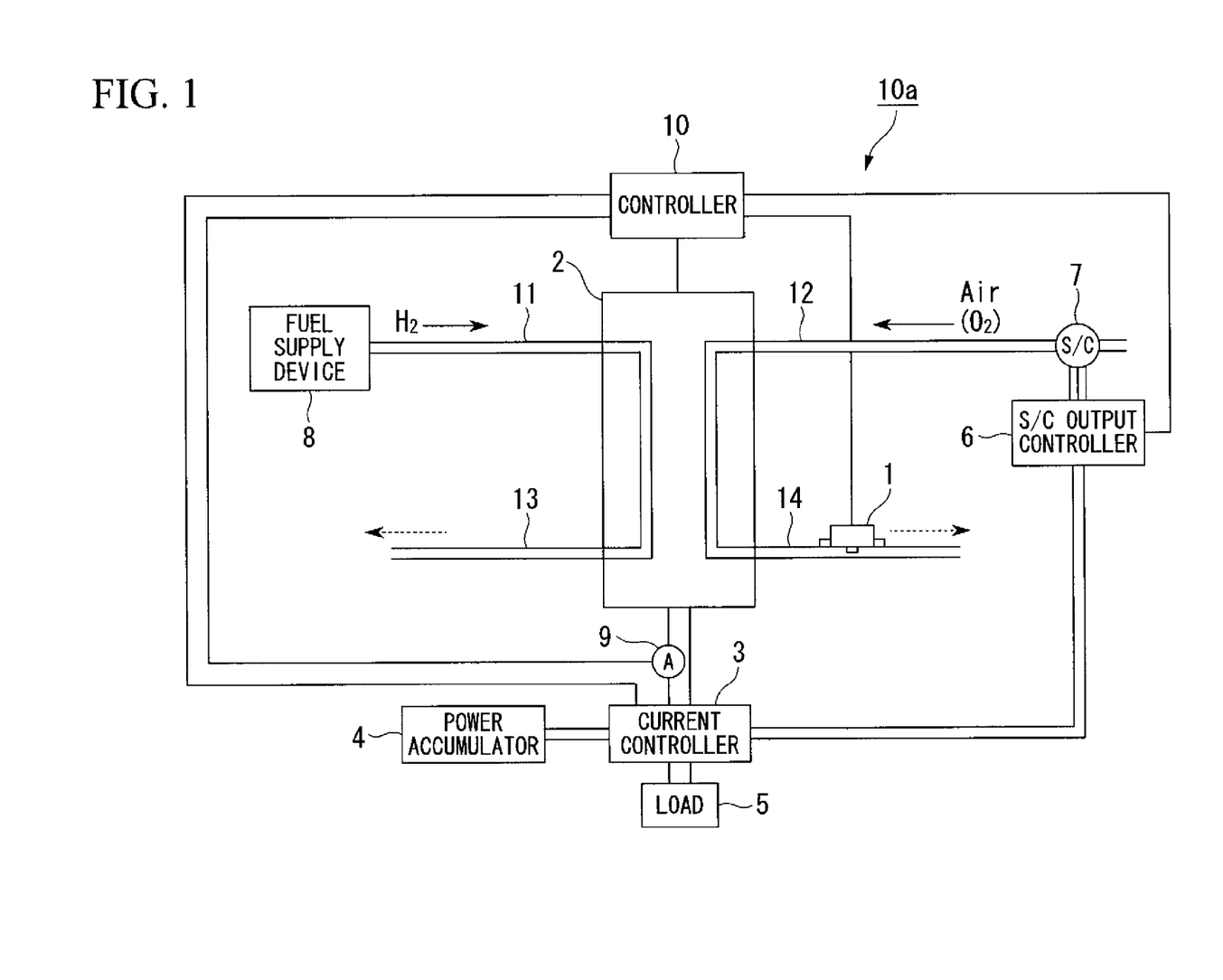
FIG. 1 is a construction view of a fuel cell system equipped with a gas sensor according to one embodiment of the present invention.

As shown in for example FIG. 1, a gas sensor 1 of the present embodiment is installed in a fuel cell system 10a. This fuel cell system 10a is provided with a fuel cell 2, a current controller 3, a power accumulator 4, a load 5, an S/C output controller 6, a super charger (S/C) 7, a fuel supply device 8, an output current sensor 9, and a controller 10. Among lines 11, 12, 13, and 14, the gas sensor 1 is provided to the outlet line 14 on an oxygen electrode side.

The fuel cell 2 is mounted as a driving source in a vehicle such as an electric vehicle. The fuel cell 2 is constituted by a plurality of cells, each cell consisting of an electrolyte electrode structure, in which a solid polymer electrolyte membrane is held between a fuel electrode and an oxygen electrode, and sandwiched by separators.

Fuel gas containing hydrogen is supplied from the fuel supply device 8 having a high-pressure tank and the like, to the inlet line 11 that is connected to the hydrogen electrode of the fuel cell 2. The hydrogen that is ionized at a catalyst electrode of the hydrogen electrode moves to the oxygen electrode through the solid polymer electrolyte membrane which is properly humidified. Electrons that are generated in accordance with the movements thereof are taken out to an outer circuit, and used as direct current energy.

Oxidizing gas such as oxygen or air is supplied from the super charger (S/C) 7 to the inlet line 12 that is connected to the oxygen electrode, and water is generated at the oxygen electrode as a result of a reaction of hydrogen ions, electrons, and oxygen. Offgas remaining after the reaction is exhausted through the outlet lines 13 and 14 from the fuel electrode and the oxygen electrode respectively.

The gas sensor 1 such as a gas-contact combustion type sensor is provided on the upper side of the outlet line 14 on the oxygen electrode side. This gas sensor 1 enables confirming that the hydrogen gas is not exhausted through the outlet line 14 on the oxygen electrode side.

The super charger (S/C) 7 introduces air around the vehicle to compress it, and supplies the compressed air as a reaction gas to the oxygen electrode side of the fuel cell 2.

The rotational speed of a non-illustrated motor that drives the super charger (S/C) 7 is controlled by the S/C output controller 6 having a PWM inverter that performs, for example, pulse wave modulation (PWM), in accordance with control instruction input from the controller 10.

The generated current (the output current) extracted from the fuel cell 2 is input to the current controller 3. The current controller 3 is connected to the power accumulator 4 having a capacitor that is formed by directly connecting a plurality of capacitor cells each formed from, for example, an electric double layer condenser, an electrolytic condenser, or the like.

The fuel cell 2 and the current controller 3, and the power accumulator 4 are connected to for example: a non-illustrated traction motor; the load 5 formed from auxiliary equipments such as a non-illustrated cooler and a non-illustrated air conditioner of for example the fuel cell 2 and the power accumulator 4; and the S/C output controller 6, in a parallel manner.

In this fuel cell system 10a, the controller 10 outputs instruction values for the flow rates of the air supplied from the super charger (S/C) 7 to the fuel cell 2, and for the flow rate of the fuel gas supplied from the fuel supply device 8 to the fuel cell 2, based on, for example, the driving state of the vehicle, the hydrogen concentration in the fuel gas supplied to the hydrogen electrode of the fuel cell 2, the hydrogen concentration in the offgas exhausted from the hydrogen electrode of the fuel cell 2, and the power generating state of the fuel cell 2 (i.e., the voltage between terminals of the plural fuel cells for example, the output current extracted from the fuel cell 2, and the like). In this manner, the controller 10 controls the power generating state of the fuel cell 2.

Therefore, the controller 10 is input with measurement signal output from the output current sensor 9 that measures the output current generated from the fuel cell 2.

Furthermore, in the controller 10, the current controller 3 controls the value of the output current generated by the fuel cell 2, in accordance with power generation instruction (i.e., FC output instruction value) to the fuel cell 2.

Figure 2:
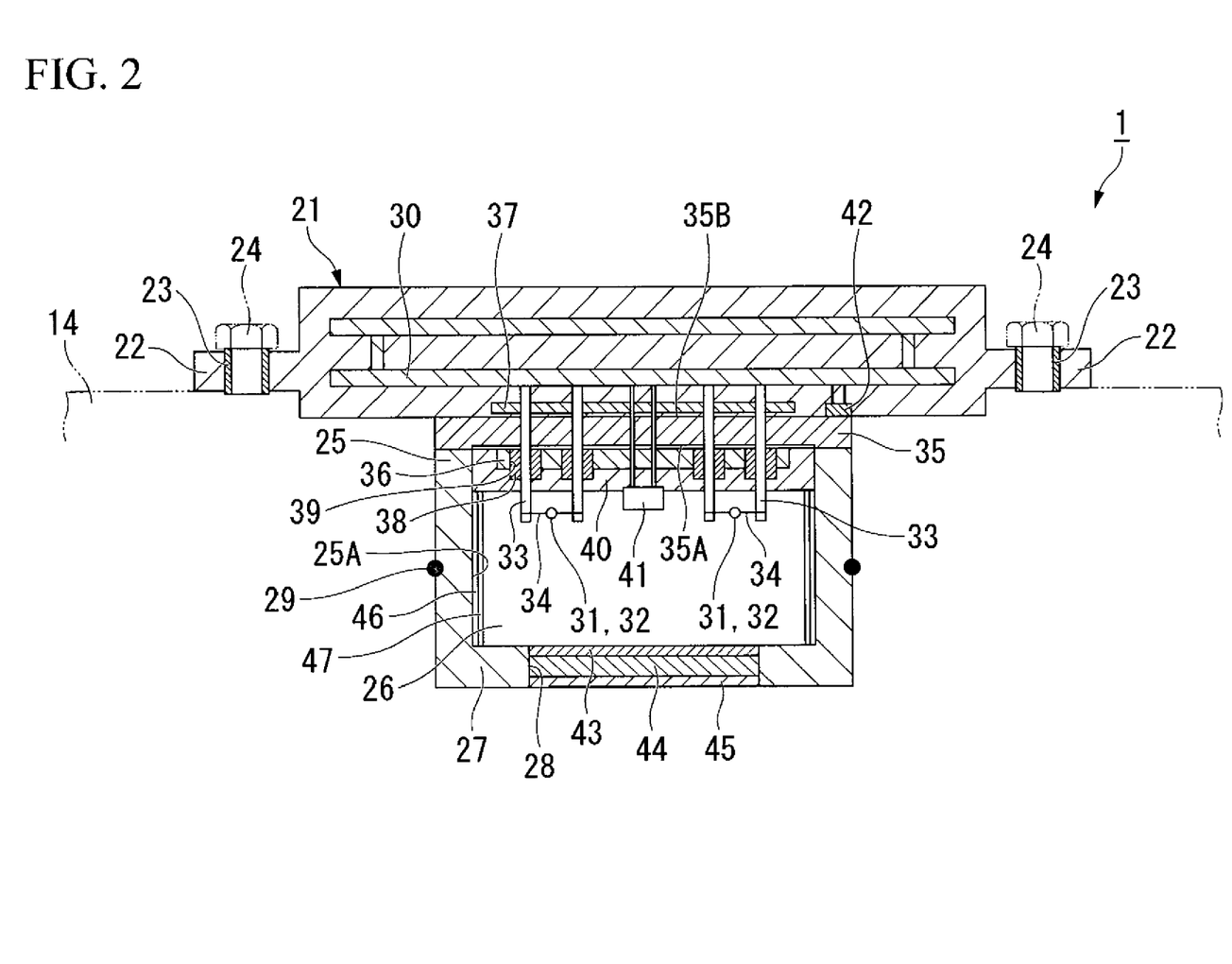
FIG. 2 is a side sectional view of the gas sensor.

As shown in FIG. 2, the gas sensor 1 is provided with a rectangular shaped case 21 that extends along the length of the outlet line 14. The case 21 is made from, for example, polyphenylene sulfide, and has flange portions 22 on the both sides in the length thereof. Each of the flange portions 22 has a collar 23 therein, and is fixed to attachment faces of the outlet line 14 by screwing bolts 24 inserted in the collars 23.

A ceramic-made cylinder member 25 is provided on one face of the case 21 in the thickness thereof, via an aftermentioned base member 35. This cylinder member 25 is inserted from the exterior of the outlet line 14 into a penetration hole formed in the outlet line 14.

The inside of the cylinder member 25 is formed as a gas detection chamber 26. A ceramic-made flange member 27 is unitarily formed along the inside wall of the gas detection chamber 26, and the center of the flange member 27 has a penetration that forms a gas introducing section 28. A sealing member 29 is attached onto the exterior of the cylinder member 25, and fittingly contacts the inner wall of the penetration hole in the outlet line 14 to secure the airtightness.

A circuit board 30 packed with resin material is provided in the case 21, and is connected to for example two pairs of a detection element 31 and a temperature correction element 32 arranged in the gas detection chamber 26, via a plurality of stays 33 (a supporting member) that are connected to the circuit board 30 as electrical paths, and lead wires 34.

The stays 33 being the electrical paths penetrate the substantially ring plate-shaped base member 35 arranged between the case 21 and the cylinder member 25. The bottom ends of the stays 33 are connected to the circuit board 30 in the case 21, while the distal ends of the stays 33 are fixed to the base member 35 so as to protrude into the gas detection chamber 26.

The base member 35 is a plate member formed from insulation material such as alumina, glass epoxy, or the like. A plate-shaped heater 36 such as a PTC (positive temperature coefficient) thermistor formed from for example barium titanate or the like is provided on a surface 35A of the base member 35 on the gas detection chamber 26 side. On a back face 35B of the base member 35, it is provided with a back side heater 37 that is formed by printing and burning for example a conductive resistance (for example, conductive metals of silvers or palladiums, or the like), and that forms a conductive pattern of a portion of the electrical circuit. By heating the base member 35 from both of the surface side and the back side thereof with the heaters 36 and 37, it is possible to prevent increasing the temperature difference between the surface side and the back side of the base member 35, and thereby enabling suppressing dew condensation produced on the gas detection chamber 26 side and preventing thermal deformation of the base member 35.

Moreover, the plate-shaped heater 36 has an external shape of for example a disc, and has electrical terminals on the both ends in the diameter thereof as electrical paths.

When a PTC thermistor is employed as the plate-shaped heater 36, the Curie temperature can be set to an arbitrary value by arranging the material compositions of the semiconductor ceramic that is mainly formed from barium titanate and forms the PTC thermistor. For example, the plate-shaped heater 36 can be a constant temperature heater, by utilizing the characteristics in which the electrical resistance suddenly decreases from the Curie temperature.

That is, the PTC thermistor generates heat by a Joule heat generated by applying the voltage onto a PTC element, the resistance of the PTC element increases on the order of logarithm when the temperature of the PTC element exceeds the Curie temperature. With this, the current supplied to the PTC element decreases and thereby suppressing increasing the voltage; therefore, the heating temperature thereof will be reduced. On the other hand, when the resistance of the PTC element decreases, the current supplied to the PTC element will increase to increase the electrical power again, and thereby increasing the heating temperature. In addition, when the resistance of the PTC element decreases, the current passing though the PTC element will increase to increase the electrical power again, and thereby increasing the heating temperature. By repeating this series of operations, the PTC thermistor will work as a constant temperature heater having a self-controlling function.

In addition, terminal pedestals 38 for positioning that are formed by mold injection and thermosetting of resins such as polyphenylene sulfide (PPS), polybutylene terephthalate (PBT), phenol, epoxy, or the like, are provided on each of the stays 33 that are formed from combined metal of copper alloy, alloy, nickel alloy, or the like, at the predetermined position along the length of the stays 33.

The strays 33 are arranged such that the positions of the protruding distal ends of the strays 33 are set to be the predetermined position in the gas detection chamber 26, by fixing the stays 33 to the base member 35 while in a state where the terminal pedestals 38 of the stays 33 are attached in the penetration holes 39 formed in the plate-shaped heater 36 on the surface side of the base member 35. Moreover, since the terminal pedestals 38 are provided to each of the stays 33, it is possible to suppress overheating of the stays 33 due to the heat of the plate-shaped heater 36.

Moreover, if the electric circuit is formed by for example printing, etching, or the like, on the surface of the insulative base member 35, the electrical circuit and the strays 33 may be connected by soldering, welding, or the like.

Furthermore, in the gas detection chamber 26, a covering layer 40 made from resin such as epoxy is provided so as to cover the surfaces of the plate-shaped heater 36 and the stays 33, and the distal ends of the stays 33 protrude from the covering layer 40. With this construction, the plate-shaped heater 36 can be prevented from contacting with water.

A status monitoring sensor 41 for measuring the temperature and the humidity around the elements 31 and 32 in the gas detection chamber 26 is fixed by the covering layer 40, and is connected to the circuit board 30 in the case 21.

A temperature sensor 42 for measuring the temperature around the position of the gas sensor 1 is provided on an end of the back face 35B of the base member 35, and is connected to the circuit board 30 in the case 21.

In the gas introducing section 28, along the direction from the bottom end to the distal end in the thickness of the gas sensor 1, it is arranged with: a reticular or porous explosion-proof member 43 (for example, a sintered filter) formed from for example metal or ceramic; an inlet heater 44 such as the PTC thermistor, that is porous or has a plurality of communication holes; and a water-repellent filter 45 formed from resin or the like. With this construction, the examination gas from the outside is sequentially passes through the water-repellent filter 45, the inlet heater 44, and the explosion-proof member 43, and is then introduced into the gas detection chamber 26. In this manner, examination gas can be maintained at the temperature that is higher than the dew point temperature. Furthermore, the explosion-proof member 43 can be directly heated by contacting to the inlet heater 44, and thereby enabling preventing producing dew condensation in the explosion-proof member 43.

An inner wall surface 25A of the cylinder member 25 is covered with a metal plate 46, and the surface of the metal plate 46 is covered with a water-repellent layer 47. With this metal plate 46, it is possible to provide a region in the gas detection chamber 26, where is away from the elements 31 and 32, and dew condensation is relatively easily produced due to the gravity. Furthermore, dew condensation produced around the metal plate 46 moves vertically downward by the water-repellent layer 47 (i.e., toward the gas introducing section 28), and thereby preventing contacting with the elements 31 and 32.

Moreover, the detection elements 31 are a known element, and are formed by covering the surface of a coil of a metal line which contains platinum having a high temperature coefficient to electric resistance, etc., with a carrier such as alumina which carries a catalyst consisting of noble metals, etc., which are reactive to the hydrogen (i.e., the detection target gas).

The temperature correction elements 32 are not reactive to the detection target gas, and are constituted by, for example, covering the surface of a coil which is equivalent to the coil of the detection element 31, with a carrier such as alumina, so as to form a substantially ball-shape.

The gas sensor 1 can detect the hydrogen concentration by (i) using the difference in electrical resistance generated between the detection elements 31 which reach a high temperature by a heat generation due to the burning reaction generated when hydrogen which is the detection target gas comes into contact with the catalyst of the detection elements 31, and the temperature correction elements 32 having a temperature lower than that of the detection elements 31 due to no burning reaction with the detection target gas, and (ii) canceling the change in electrical resistance due to atmospheric temperature.

In accordance with for example the driving state of the fuel cell 2 or the like, the controller 10 controls operating conditions of the gas sensor 1 and the heaters 36, 37, and 44 (for example, each timings of starting and stopping of the operation), and also controls the power supplying status to for example the detection elements 31, the temperature correction elements 32, and each heaters 36, 37, and 44.

The controller 10 controls the electrical power supplied to the heaters 36, 37, and 44, based on the temperature measured by the status monitoring sensor 41 and the temperature sensor 42. For example, while in an operation or the like of the fuel cell 2, the controller 10 controls the temperature and the humidity inside the gas detection chamber 26 measured by the status monitoring sensor 41 to be a values within the predetermined ranges that suppresses producing of the dew condensation. In addition, the controller 10 controls such that: if the temperature sensor 42 measures the relatively lower temperature, then the electrical power is supplied to the heaters 36, 37, and 44; and if the temperature sensor 42 measures the relatively higher temperature, then the supply of the electrical power to the heaters 36, 37, and 44 is stopped to suppress the excessively increasing the power consumption.

At this time, the controller 10 controls the amount of electricity supplied to the heaters 36, 37, and 44 by, for example, feedback control of the current value supplied to the heaters 36, 37, and 44, or by chopper control based on, for example, on/off operations of a switching element (that is, on/off switching control of the electricity supplied to the heater 36, 37, and 44) or the like.

As has been explained in the above, according to the gas sensor 1 of the present embodiment, the stays 33 that support the elements 31 and 32 are fixed so as to protrude from the plate-shaped heater 36 provided to the base member 35; therefore, it is possible to directly heat the base member 35 and the stays 33 connected to the elements 31 and 32. With this configuration, even when the electrical power to the elements 31 and 32 is stopped, it is possible to prevent producing dew condensation at the stays 33 and the base member 35 in additions to the elements 31 and 32 themselves. Furthermore, even when dew condensation is produced at other locations inside the gas sensor 1, it is possible to prevent the dew condensation reaching to the elements 31 and 32 through the stays 33; therefore, it is possible to prevent destructions and deteriorations of the elements 31 and 32 due to the dew condensation contacting with the elements 31 and 32. Accordingly, it is possible to improve the durability of the elements 31 and 32, and to increase the detection accuracy of the gas sensor 1.

Moreover, in the present embodiment, the gas-contact combustion-type sensor is used for the gas sensor 1; however, the gas sensor 1 is not limited to the gas-contact combustion-type sensor, and other types of sensors may be used such as a semiconductor type sensor that measures the gas concentration in accordance with an element resistance that is produced when the detection target gas contacts to and depart from oxygen on a surface of the detection element.

Figure 3:
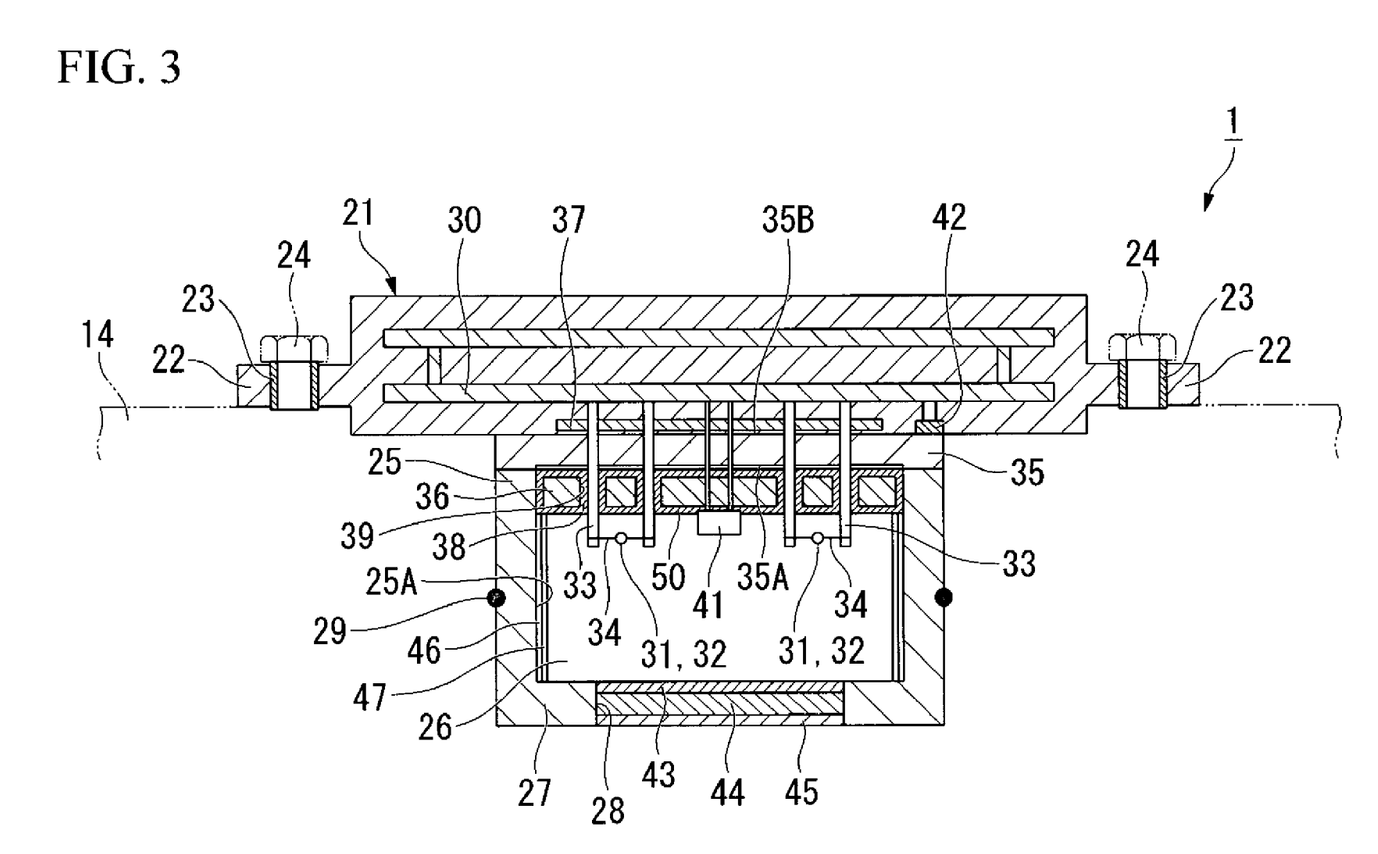
FIG. 3 is a side sectional view of a gas sensor according to a variant example of the present embodiment.

Moreover, in the above-mentioned embodiment, the covering layer 40 is provided so as to cover the surfaces of the plate-shaped heater 36 and the terminal pedestals 38 of the stays 33; however, it is not limited to this construction, and the entire surface of the plate-shaped heater 36 may be covered with a covering layer 50 made of resin such as epoxy or the like. In this case, as shown in for example FIG. 3, the terminal pedestals 38 of the stays 33 may be unitarily formed with the covering layer 50.

In addition, the gas sensor 1 of the present embodiment employs the covering layer 40; however, it is not limited to this configuration, and the covering layer 40 may be omitted.

Moreover, in the present embodiment, the PTC thermistor is used for the plate-shaped heater 36; however, it is not limited to the PTC thermistor, and other heaters such as a sintered compact heater, a heater that is formed by printing and burning a conductive resistor on the surface of the base member 35 to form a conductive pattern of a part of the electric circuit, or the like may be employed thereinstead.

Moreover, in the present embodiment, the gas sensor 1 is provided with the status monitoring sensor 41 and the temperature sensor 42; however, the construction thereof is not limited to this, and may be arranged such that the temperature sensor 42, or both of the status monitoring sensor 41 and the temperature sensor 42 may be omitted.

Moreover, in the present embodiment the explosion-proof member 43, the inlet heater 44, and the water-repellent filter 45 are provided in the gas introducing section 28; however, the construction is not limited to this, and may be arranged such that at least one of the explosion-proof member 43 and the water-repellent filter 45 may be omitted.

Figure 4:
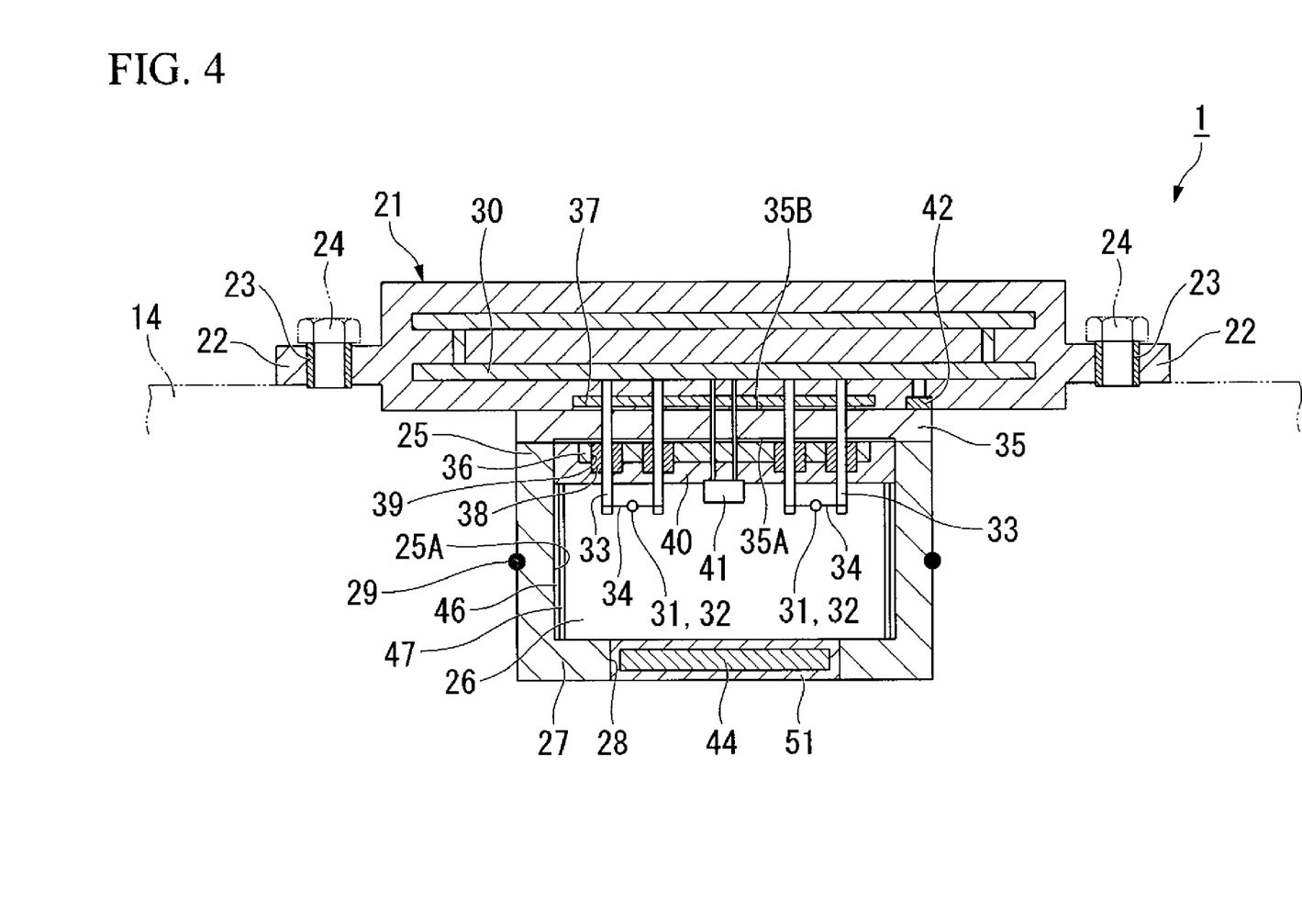
FIG. 4 is a side sectional view of a gas sensor according to a variant example of the present embodiment.
Figure 5:
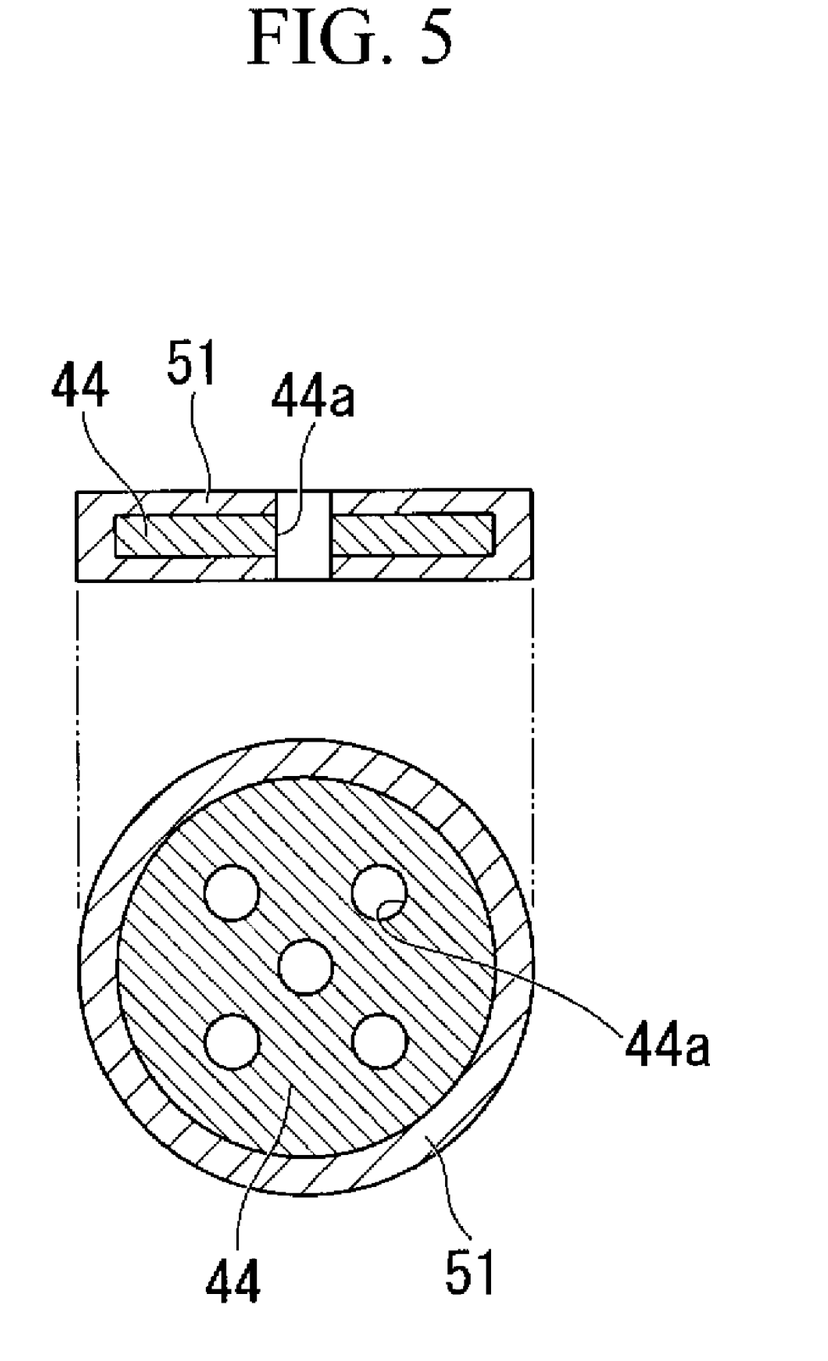
FIG. 5 is a side sectional view of a heater provided in a gas introducing section of the gas sensor according to the variant example of the present embodiment.

In addition, in the present embodiment, as shown in FIG. 4, the entire surface of the inlet heater 44 may be covered with a covering layer 51 made of resin such as epoxy or the like. In this case, as shown in FIG. 5, a plurality of communication holes 44a that penetrate in the thickness of the inlet heater 44 are formed in the inlet heater 44. The inlet heater 44 provided with the covering layer 51 is fixed into the gas introducing section 28 by ultrasonic welding, an epoxy adhesive, or the like.

Figure 6:
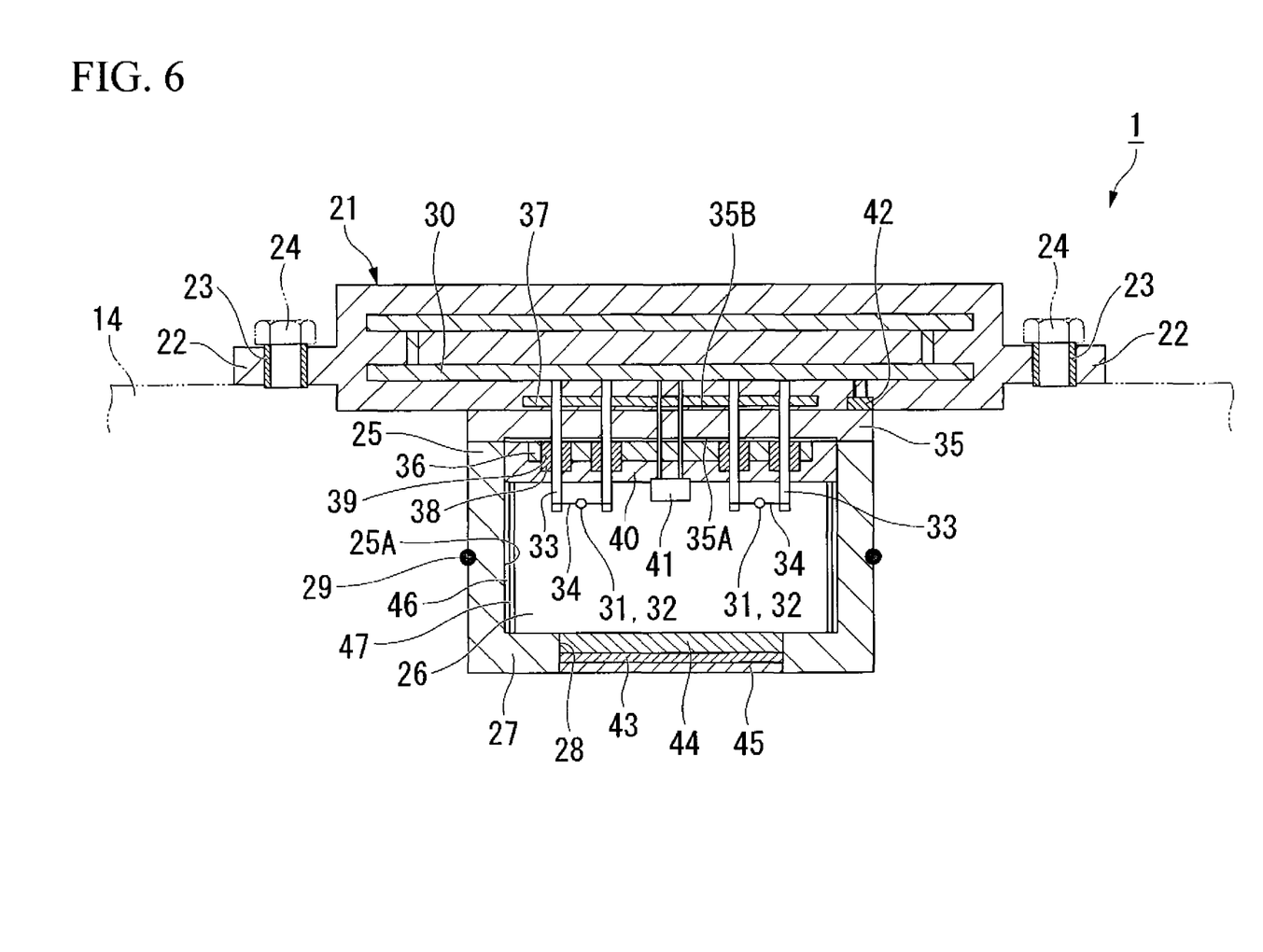
FIG. 6 is a side sectional view of a gas sensor according to a variant example of the present embodiment.
Figure 7:
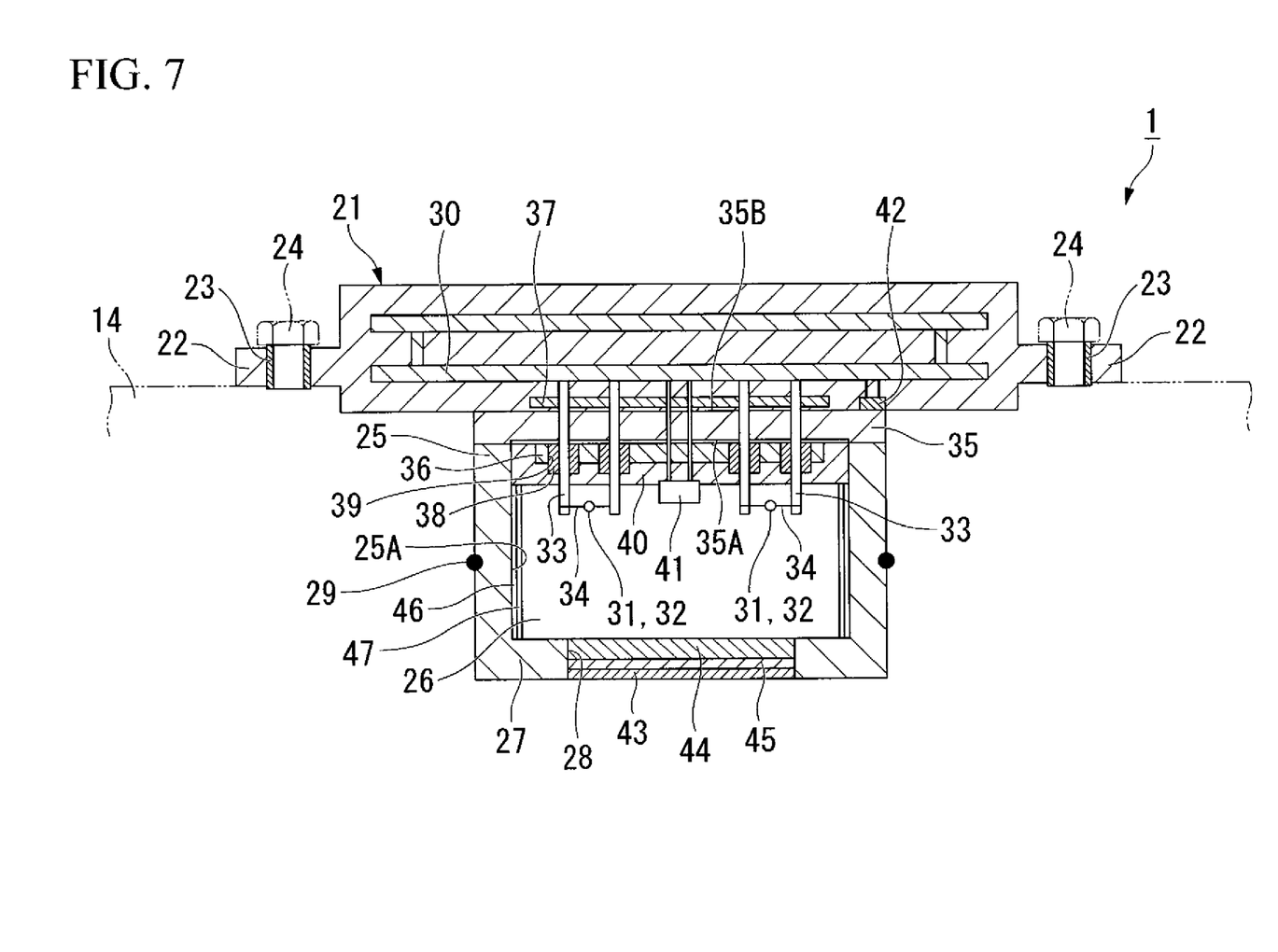
FIG. 7 is a side sectional view of a gas sensor according to a variant example of the present embodiment.
Figure 8:
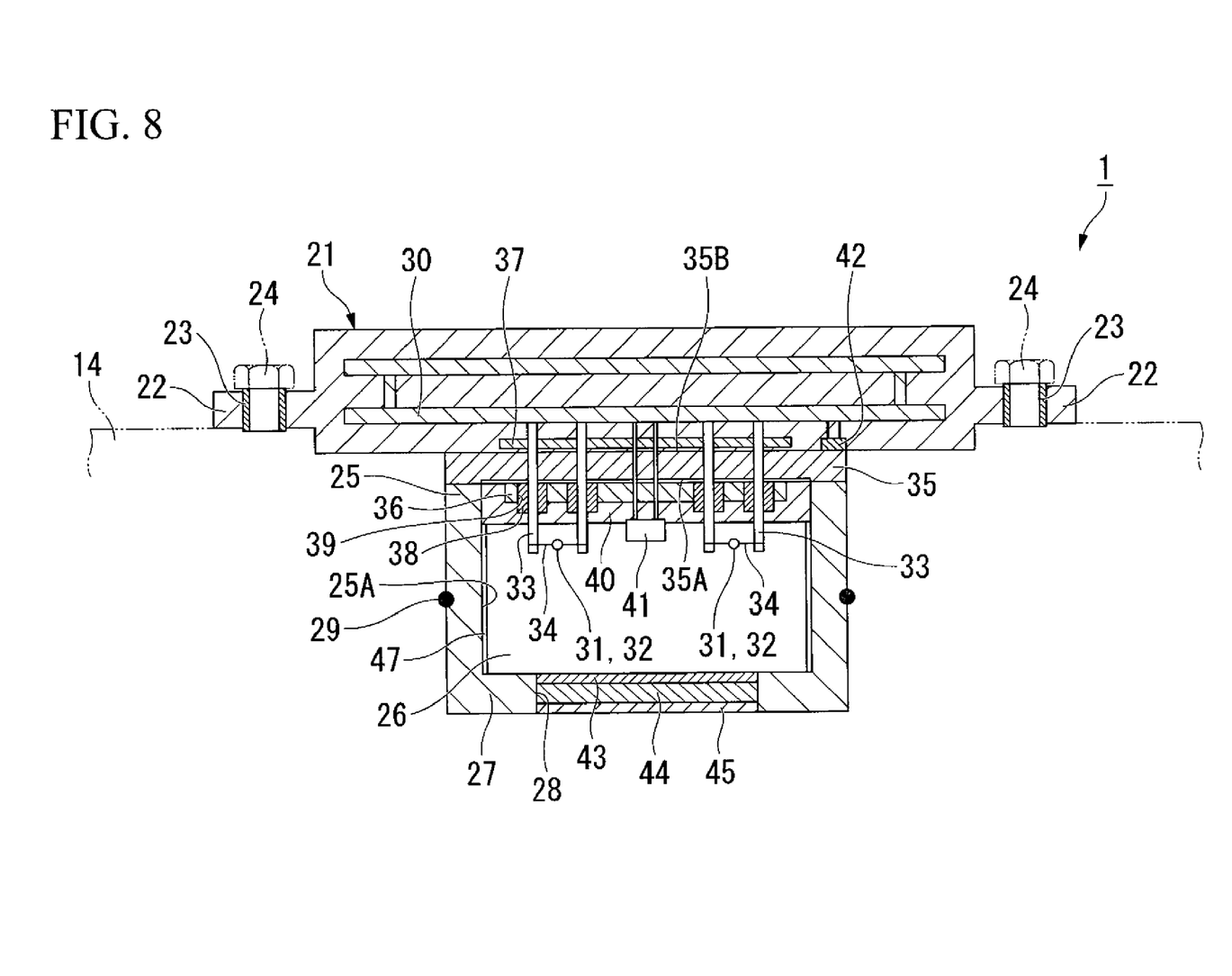
FIG. 8 is a side sectional view of a gas sensor according to a variant example of the present embodiment.

In addition, in the present embodiment, the explosion-proof member 43, the inlet heater 44, and the water-repellent filter 45 are sequentially arranged along the thickness of the gas sensor 1 from the bottom to the distal thereof; however, the construction is not limited to this, and may be arranged such that, as shown in FIG. 6, the inlet heater 44, the explosion-proof member 43, and the water-repellent filter 45 are sequentially arranged along the thickness of the gas sensor 1 from the bottom to the distal thereof. Otherwise, as shown in FIG. 7, the inlet heater 44, the water-repellent filter 45, and the explosion-proof member 43 may be sequentially arranged along the thickness of the gas sensor 1 from the bottom to the distal thereof.

Moreover, in the present embodiment, the metal plate 46 and the water-repellent layer 47 are provided on the inner wall surface 25A of the cylinder member 25; however, the construction is not limited to this, and may be arranged such that the metal plate 46 is omitted and only the water-repellent layer 47 is provided on the inner wall surface 25A of the cylinder member 25.

In addition, in the present embodiment, in accordance with the necessity, a hydrophilic layer may be provided instead of the water-repellent layer 47.

Moreover, in the present embodiment, the back side heater 37 formed by printing and burning for example a conductive resistance, is provided on the back face 35B of the base member 35; however, the construction is not limited to this, and other heaters such as the PTC thermistor, a sintered heater, or the like may be employed thereinstead. Otherwise, if the base member 35 is made of glass epoxy or the like, it may be arranged such that the back side heater 37 is formed by printing it on a surface of a ceramic, and attaching the ceramic onto the base member 35 using soldering, metal bonding, or the like.

Moreover, in the present embodiment, a sealing material may be arranged between the base member 35 and the cylinder member 25 to keep the airtightness.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A gas sensor, comprising:
   a detection element that measures a gas concentration of a detection target gas contained in an examination gas;

a substrate having a first heating element; and at least one supporting member that is fixed to the substrate, protrudes from the heating element towards a gas inlet port, and supports the detection element, wherein said substrate is a top face of a gas detection chamber into which the examination gas is introduced; and wherein the supporting member supports the detection element so as to protrude downward from the substrate, wherein an inner surface of a cylinder member that forms the detection chamber is made of a metal plate, thereby forming an area, at a position away from the detection element, where dew condensation is produced, and wherein the inner surface of the metal plate is covered with a water-repellent layer.

2. The gas sensor according to claim 1, wherein the supporting member is made of a metal.

3. The gas sensor according to claim 2, wherein the detection element has a substantially ball shape, and wherein the detection element is connected to a pair of said supporting members via a lead wire.

4. The gas sensor according to claim 1, wherein said gas inlet port of a gas detection chamber into which the examination gas is introduced is provided with a second heating element having a communication hole.

5. The gas sensor according to claim 4, wherein the gas inlet port is provided below the gas detection chamber; and wherein an explosion-proof member, the second heating element, and a water-repellent filter are arranged in order from an inside to an outside of the gas detection chamber.

6. The gas sensor according to claim 1, wherein a surface heater is provided on a front surface of the substrate, and wherein a back face heater is provided on a back face of the substrate.

7. The gas sensor according to claim 1, wherein the first heating element is a PTC thermistor.

8. The gas sensor according to claim 1, wherein said gas inlet port of a gas detection chamber into which the examination gas is introduced is provided with a porous heating element.

* * * * *